(12) United States Patent
Field et al.

(10) Patent No.: US 8,506,504 B2
(45) Date of Patent: Aug. 13, 2013

(54) BIOPSY DEVICE HAVING SPECIMEN LENGTH ADJUSTMENT ASSEMBLY INCLUDING THROW STOP ADJUSTABLE BY ROTATION OF DISTAL NOSE ON HOUSING

(75) Inventors: Steven E. Field, Grand Rapids, MI (US); Chad J. Bacon, Coopersville, MI (US); Michael O. Bray, II, Clinton Township, MI (US); Ryan Goosen, Hudsonville, MI (US)

(73) Assignee: Inrad, Inc., Grand Rapids, MI (US)

( * ) Notice: Subject to any disclaimer, the term of this patent is extended or adjusted under 35 U.S.C. 154(b) by 0 days.

(21) Appl. No.: 13/461,252

(22) Filed: May 1, 2012

(65) Prior Publication Data

US 2012/0215130 A1 Aug. 23, 2012

Related U.S. Application Data

(62) Division of application No. 12/474,421, filed on May 29, 2009, now Pat. No. 8,197,419.

(60) Provisional application No. 61/057,378, filed on May 30, 2008.

(51) Int. Cl.
*A61B 10/00* (2006.01)
*A61B 1/00* (2006.01)

(52) U.S. Cl.
USPC .......................... 600/567; 600/568; 606/171

(58) Field of Classification Search
USPC .................. 600/564–568, 562; 606/170–171
See application file for complete search history.

(56) References Cited

U.S. PATENT DOCUMENTS

| | | | |
|---|---|---|---|
| 4,243,048 A | 1/1981 | Griffin | |
| 5,156,160 A | 10/1992 | Bennett | |
| 5,335,672 A | 8/1994 | Bennett | |
| 5,392,790 A | 2/1995 | Kanner et al. | |
| 5,916,175 A | 6/1999 | Bauer | |
| 6,083,176 A | 7/2000 | Terwilliger | |
| 6,106,484 A | 8/2000 | Terwilliger | |
| 6,165,136 A | 12/2000 | Nishtala | |
| 6,283,925 B1 | 9/2001 | Terwilliger | |
| 6,358,217 B1 | 3/2002 | Bourassa | |
| 6,749,576 B2 | 6/2004 | Bauer | |
| 7,041,065 B2 | 5/2006 | Weilandt et al. | |
| 7,131,951 B2 | 11/2006 | Angel | |
| 2006/0155210 A1 | 7/2006 | Beckman et al. | |

*Primary Examiner* — Max Hindenburg
*Assistant Examiner* — John Pani
(74) *Attorney, Agent, or Firm* — McGarry Bair PC

(57) ABSTRACT

A biopsy device having a sample size control assembly for selecting the specimen size to be collected. The sample size control assembly includes a rotatable nose on the biopsy device for actuating the operation of the sample size control assembly. A needle assembly of the biopsy device can extend through the rotatable nose. Also disclosed is a method for making a biopsy device, including coupling a tip protector to a sample size control assembly.

12 Claims, 12 Drawing Sheets

BIOPSY DEVICE HAVING SPECIMEN LENGTH ADJUSTMENT ASSEMBLY INCLUDING THROW STOP ADJUSTABLE BY ROTATION OF DISTAL NOSE ON HOUSING

CROSS-REFERENCE TO RELATED APPLICATION

This application is a divisional of U.S. patent application Ser. No. 12/474,421, filed May 29, 2009, now U.S. Pat. No. 8,197,419, issued Jun. 12, 2012 which claims the benefit of U.S. Provisional Patent Application No. 61/057,378, filed May 30, 2008, both of which are incorporated herein by reference in their entirety.

BACKGROUND OF THE INVENTION

It is frequently necessary to sample or remove a sample from a suspect tissue for testing. In humans, such a sample removal is particularly useful in the diagnosis and treatment of cancerous or pre-cancerous conditions. In the case of suspected cancer, particularly cancer of the breast, early detection and diagnosis is critical to the success of the patient's treatment and recovery.

Various techniques are available to aid in detection and diagnosis, including physical examination and imaging, such as mammography, x-ray, ultrasound, magnetic resonance imaging (MRI), and the like. When a condition is detected that suggests the possibility of cancer, a biopsy can be performed to obtain tissue samples for a complete diagnosis.

One biopsy technique frequently performed is a core biopsy, which uses a core biopsy device in which a cannula is inserted into the tissue of interest, thereby coring a biopsy sample from the tissue having a cross section similar to that of the cannula, and which is retained within the cannula. The cannula, with the biopsy sample, is then removed from the tissue, followed by cytological and/or histological analysis of the sample.

One group of core biopsy devices is based on the combination of a notched inner stylet and an outer severing cannula. The stylet is retained within the lumen of the outer cannula such that the pointed end of the stylet closes off the open end of the cannula. The stylet and cannula are advanced into the tissue mass until they are near the desired biopsy site. The stylet is then advanced relative to the outer cannula to expose the notch to the biopsy site where the tissue prolapses into the notch. The outer cannula is then advanced to sever the tissue in the notch. The disadvantage of this method is that it produces a small core biopsy relative to the outer cannula size since the cross section of the sample is substantially equal to the cross section of the stylet notch, which is substantially smaller than the cross section of the outer cannula. The advantage of this method is that the sample is completely severed from the tissue mass and securely retained within the notch.

Another group of core biopsy devices is based on a coring cannula in combination with a non-notched stylet. The stylet is used to plug the end of the coring cannula during the insertion of the coring cannula into the tissue adjacent the biopsy site. The coring cannula is then advanced relative to the stylet into the biopsy site to retain a sample within the coring cannula. The advantage of this device is that a full core biopsy sample is obtained. That is, the cross section of the sample is substantially equal to the cross section of the coring cannula. The full core sample provides a much larger sample which is highly advantageous.

Some biopsy devices permit the user to select the size or length of the biopsy sample obtained. One such group only allows the user to choose between predetermined sizes or discrete intervals of sizes. Other biopsy devices allow infinite adjustment within a range of possible sizes.

SUMMARY OF THE INVENTION

In one embodiment, the invention relates to a biopsy device for the percutaneous removal of a specimen from a tissue mass. The biopsy device includes a housing having a proximal end and a distal end; a sample size control assembly for selecting the specimen size to be collected, comprising an adjusting member provided within the housing, a nose rotatably mounted to the housing and projecting from the distal end, and a throw stop coupled to the adjusting member; a cannula defining a lumen having a distal end and extending through the nose; a cannula carriage provided within the housing for relative movement therewith and coupled to the cannula; a stylet having a notch and extending through the lumen; a stylet carriage provided within the housing for movement relative to the housing, and coupled to the stylet, and a firing assembly carried by the housing and operably coupled to the cannula and stylet carriages, wherein the firing assembly is configured to relatively move the cannula and the stylet from an armed position, where the cannula and stylet carriages are spaced from the throw stop and the cannula covers the notch, through an intermediate position, where the stylet carriage abuts the throw stop and the notch extends at least partially beyond the distal end of the cannula, and to a fired position, where both the cannula and stylet carriages abut the throw stop and the cannula covers the notch, wherein the length of travel of the stylet between the armed position and the intermediate position defines a throw distance that is related to the specimen size and the nose is operably coupled to the adjusting member such that rotation of the nose actuates the adjusting member to move the throw stop within the housing to adjust the throw distance, and thereby adjust the specimen size.

In yet another embodiment, the invention relates to a method of making a biopsy device having a needle assembly and a sample size control assembly for selecting the specimen size to be collected. The method comprises disposing a tip protector over the needle assembly and coupling the tip protector to the sample size control assembly, wherein movement of the tip protector operates the sample size control assembly.

DESCRIPTION OF EMBODIMENTS OF THE INVENTION

Figure 1:
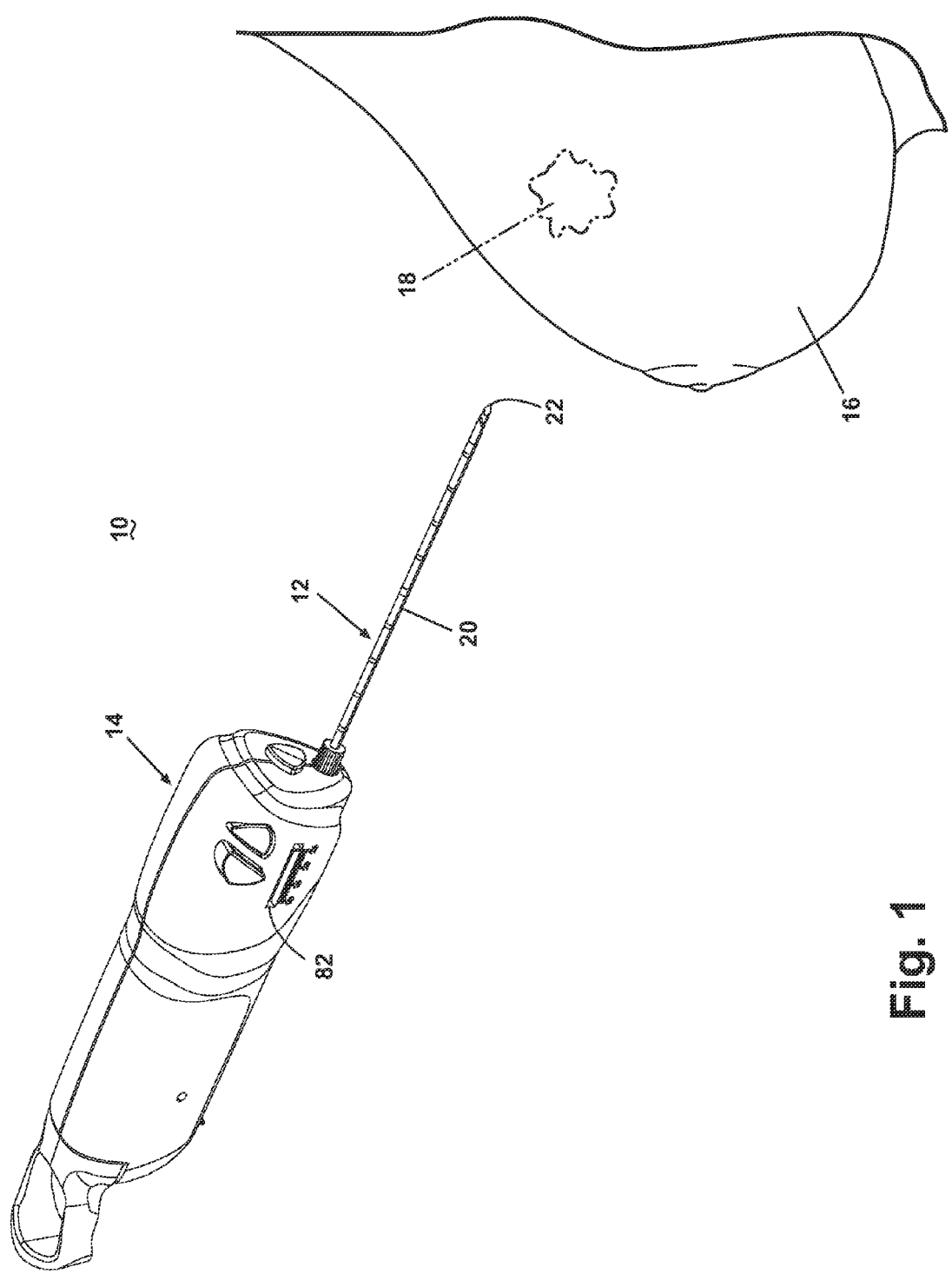
FIG. 1 is a perspective view of a lesion within a tissue mass and a biopsy device comprising a cannula assembly and an actuator assembly according to the invention for obtaining a biopsy sample from the lesion.

Referring to FIG. 1, a biopsy device 10 according to the invention is illustrated comprising a needle assembly 12 structurally and operably connected to an actuator assembly 14. The needle assembly 12 is utilized to penetrate a tissue mass 16 for obtaining a biopsy sample from a lesion 18. The needle assembly 12 can comprise a cannula 20 and a stylet 22 in coaxially telescoping relationship. While the needle assembly 12 is described herein as comprising the cannula 20 and the notched stylet 22 purposes of illustrating the operation of the biopsy device 10, it is understood that other cannula assemblies can be employed with the actuation assembly 14 of the invention. The biopsy device 10 can also optionally be characterized as a "biopsy gun". Details of the biopsy device 10 that are not specifically germane to the invention are more fully described in co-owned U.S. patent application Ser. No. 12/474,489, filed May 29, 2009, now U.S. Pat. No. 8,192,369, issued Jun. 5, 2012, entitled "Apparatus for Cocking a Biopsy Device", which is incorporated herein by reference in its entirety.

As used herein with respect to the biopsy device 10, the terms "distal" or "forward", or any variations thereof, refer to or in a direction toward the end of the needle assembly 12 and/or the actuator assembly 14 that is directed toward the lesion 18. The terms "proximal" or "rearward", or any variations thereof, refer to or in a direction toward the end of the needle assembly 12 and/or the actuator assembly 14 that is directed away the lesion 18.

The actuator assembly 14 comprises a hand-held device capable of controlling the acquisition and removal of the biopsy sample, alternately referred to as a biopsy specimen, from the lesion 18 through the cocking and firing of the cannula assembly 12. As illustrated, the cocking is manual and the firing is automated. The actuator assembly 14 is capable of cocking the cannula 20 and stylet 22 independently. The actuator assembly 14 has the additional capability of firing the cannula 20 and stylet 22 with one triggering action, or firing the cannula 20 and stylet 22 independently. The actuator assembly 14 also functions as a handle for the biopsy device 10.

Figure 2:
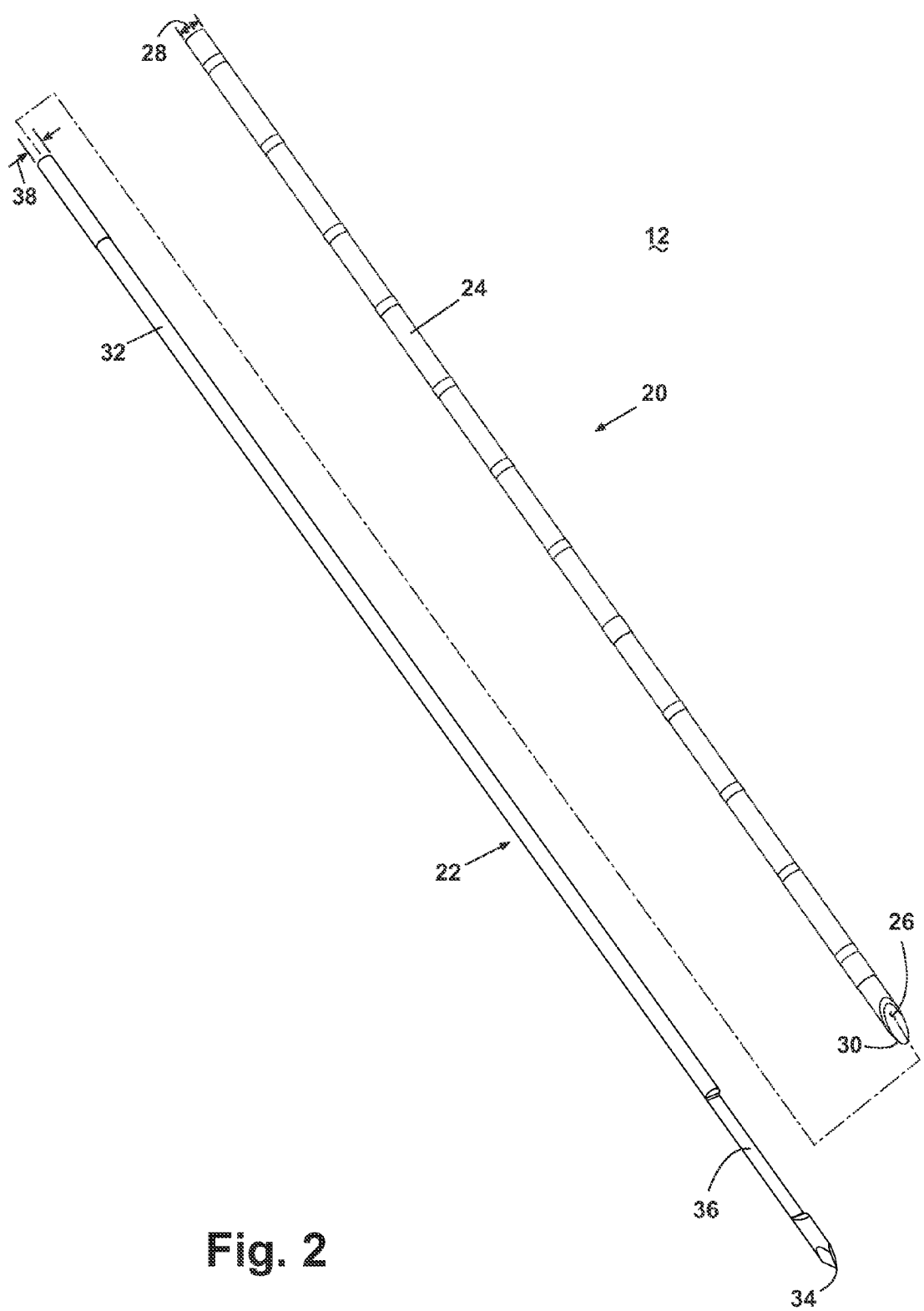
FIG. 2 is an exploded view of the cannula assembly illustrated in FIG. 1, the cannula assembly comprising a cannula and a stylet.

Referring to FIG. 2, the cannula 20 is an elongated, tubular member having an annular wall 24 defining a lumen 26 therethrough having an inner diameter 28. The cannula 20 terminates at a distal end in a cutting edge 30. The stylet 22 is an elongated, usually solid, cylindrical member comprising a stylet body 32 terminating in a pointed distal penetration tip 34. As illustrated, the penetration tip 34 is shown as comprising a trochar point; however, the penetration tip 34 can have other conventional configurations, such as a bevel point. The stylet body 32 can include a notch 36 near the distal penetration tip 34. The stylet body 32 has a constant outer diameter 38 which is somewhat smaller than the inner diameter 28 of the cannula 20 so that the stylet 22 is slidably received within the lumen 26 of the cannula 20.

Figure 3:
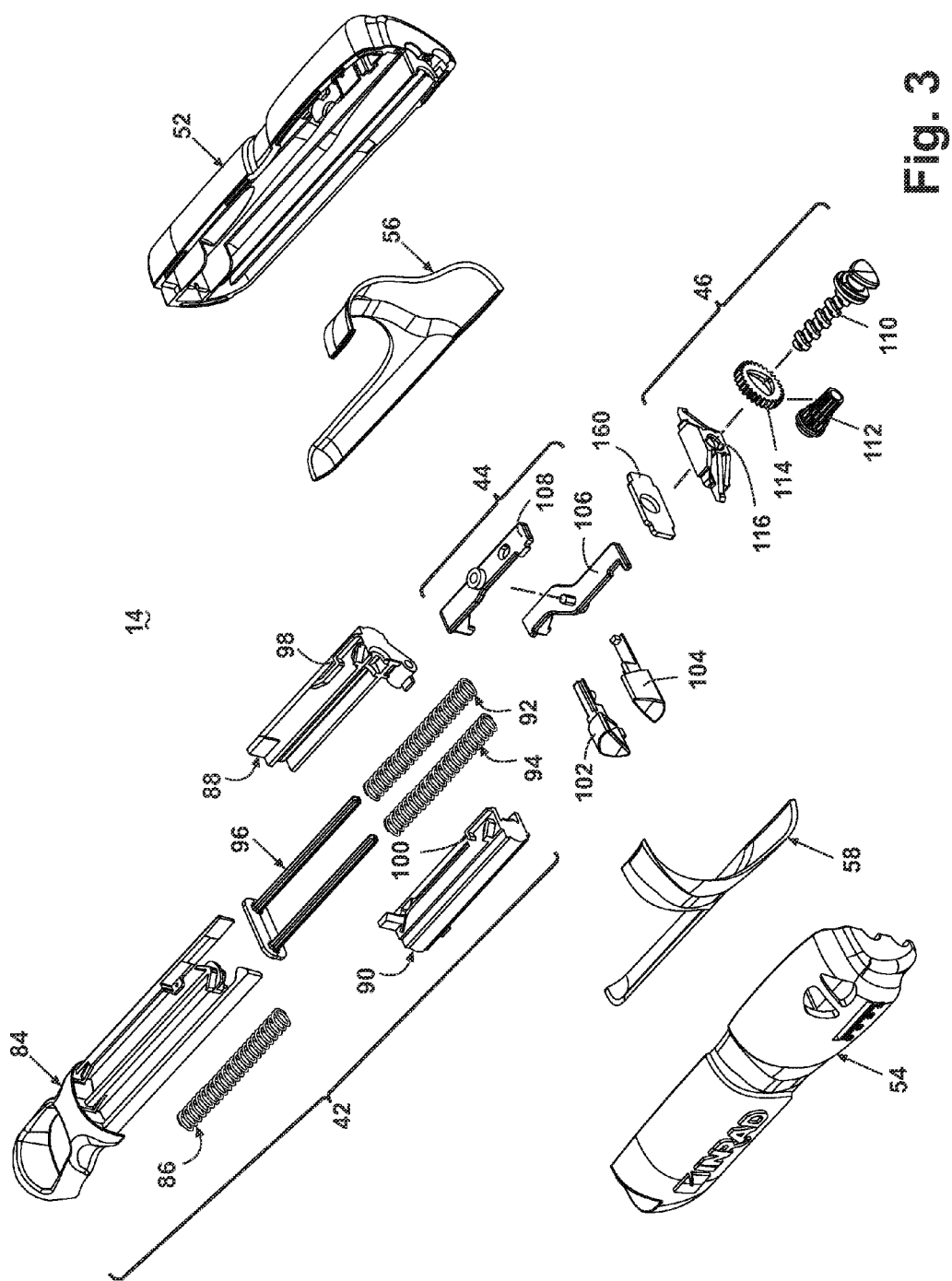
FIG. 3 is an exploded view of the actuator assembly illustrated in FIG. 1.
Figure 4:
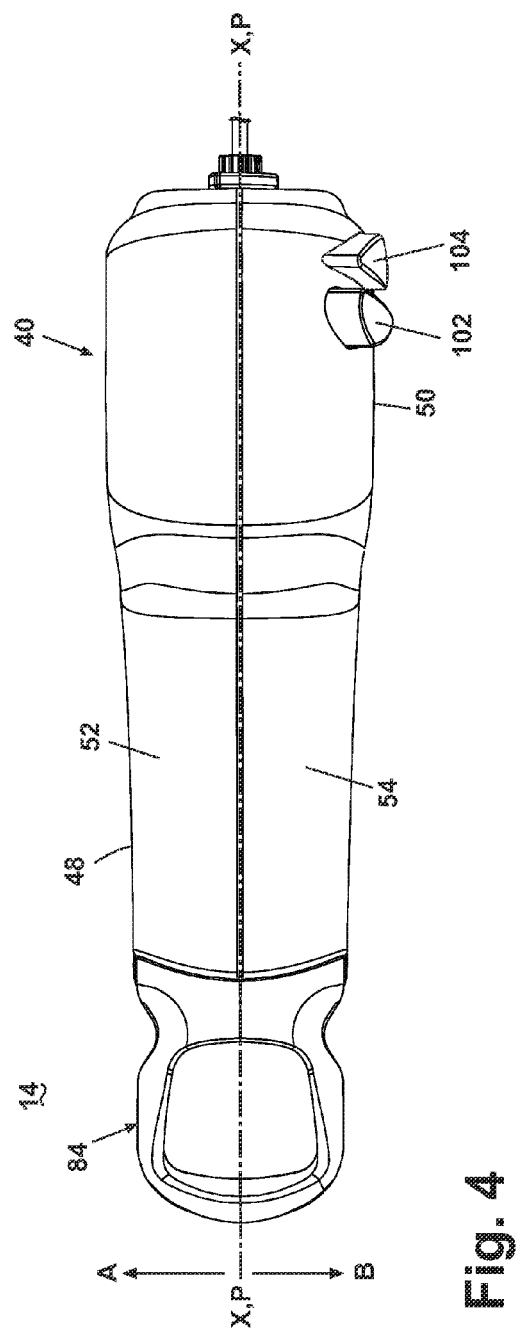
FIG. 4 is a top view of the actuator assembly illustrated in FIG. 1

Referring to FIGS. 3-4, the actuator assembly 14 comprises an outer housing 40 that supports the needle assembly 12 and both the internal and external components of the actuator assembly 14, including a cocking/firing assembly 42, a trigger assembly 44 and a sample size control assembly 46. The outer housing 40 is shaped to provide a rear grip portion 48 to provide an ergonomic, functional handle for facilitating the insertion of the needle assembly 12 into the tissue mass 16 and the recovery of a biopsy sample and an enlarged front bearing portion 50 against which the user's hand or fingers can bear to securely grip the actuator assembly 14. The outer housing 40 includes a right housing shell 52 and a left housing shell 54 adapted for cooperative registry. Each housing shell 52, 54 can have a respective overmolded section 56, 58 to provide a soft tough grip on the outer housing 40. As illustrated herein, the overmolded sections 56, 58 can be shaped to encircle the portion of the outer housing 40 where the user is likely to place their thumb and extend along the bottom side of the outer housing 40 where the user is likely to place their fingers or the palm of their hand.

Figure 5:
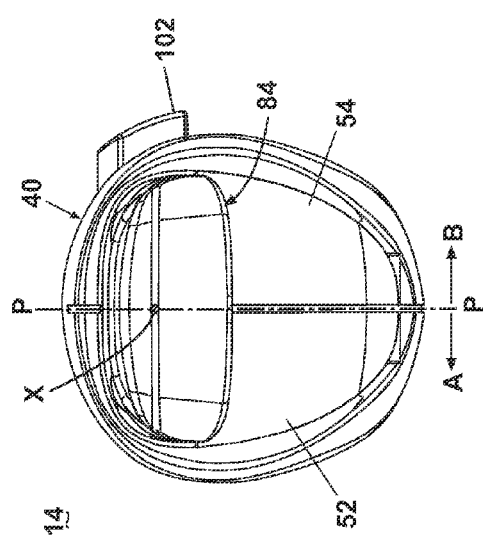
FIG. 5 is a back view of the actuator assembly illustrated in FIG. 1.

Referring to FIGS. 4-5, the outer housing 40 can comprise an operational axis X. The operational axis X can be located on an operational plane P extending through the outer housing 40. The operational plane P can be oriented vertically and can be located along the centerline of the biopsy device, therefore locating the operational axis X along the centerline of the biopsy device. The operational axis X can extend generally horizontally along the operational plane P.

While the operational axis X is illustrated extending along the centerline of the biopsy device 10, it may be off the centerline depending on the configuration of the biopsy device 10. Similarly, the operational plane P may also be oriented non-vertically. It may be horizontal or somewhere between vertical and horizontal.

Figure 6:
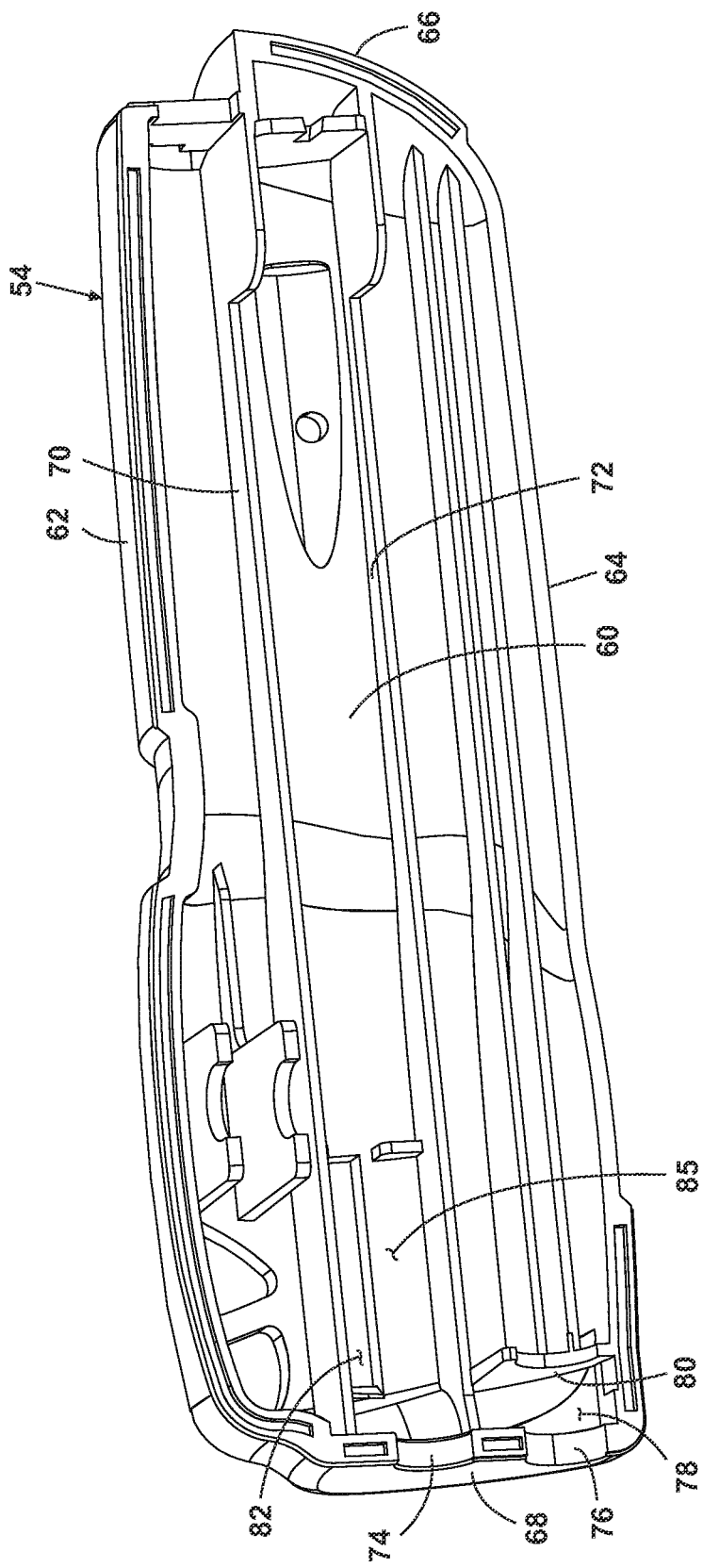
FIG. 6 is a perspective view of a left housing shell of the actuator assembly.

Referring to FIG. 6, the left housing shell 54, which is an irregularly-shaped, elongated body, comprises an elongated sidewall 60 joined to a top wall 62, a bottom wall 64, a proximal wall 66, and a distal wall 68. The walls are contoured, and configured with openings, bosses, rails, and the like, for operational support of the elements comprising the biopsy device 10. The right housing shell 52 is generally a mirror image of the left housing shell 54, and has many of the same structural elements of the left housing shell 54 arranged for cooperative registry of the structural elements in both shells 52, 54 to provide support and movement functionality to the assembled outer housing 40. Accordingly, the term "chamber" as used in the description of the left housing shell 54, unless otherwise noted, is used with the understanding that any such chamber is formed between structural elements of the assembled housing shells 52, 54.

Regarding operational support of the elements comprising the sample size control assembly, the left housing shell 54 comprises an upper guide rail 70 and a lower guide rail 72 in parallel, spaced-apart juxtaposition extending inwardly from the sidewall 60 between the proximal and distal walls 66, 68. The left housing shell 54 further comprises an upper aperture 74 and a lower aperture 76 formed in the distal wall 68. The lower aperture 76 opens into a chamber 78 extending from the distal wall 68 to a retaining wall 80 that is spaced from the distal wall 68. An elongated indicator window 82 is formed in the sidewall 60 between the guide rails 70, 72. The guide rails 70, 72 define a channel 85 adjacent the indicator window 82.

Figure 9:
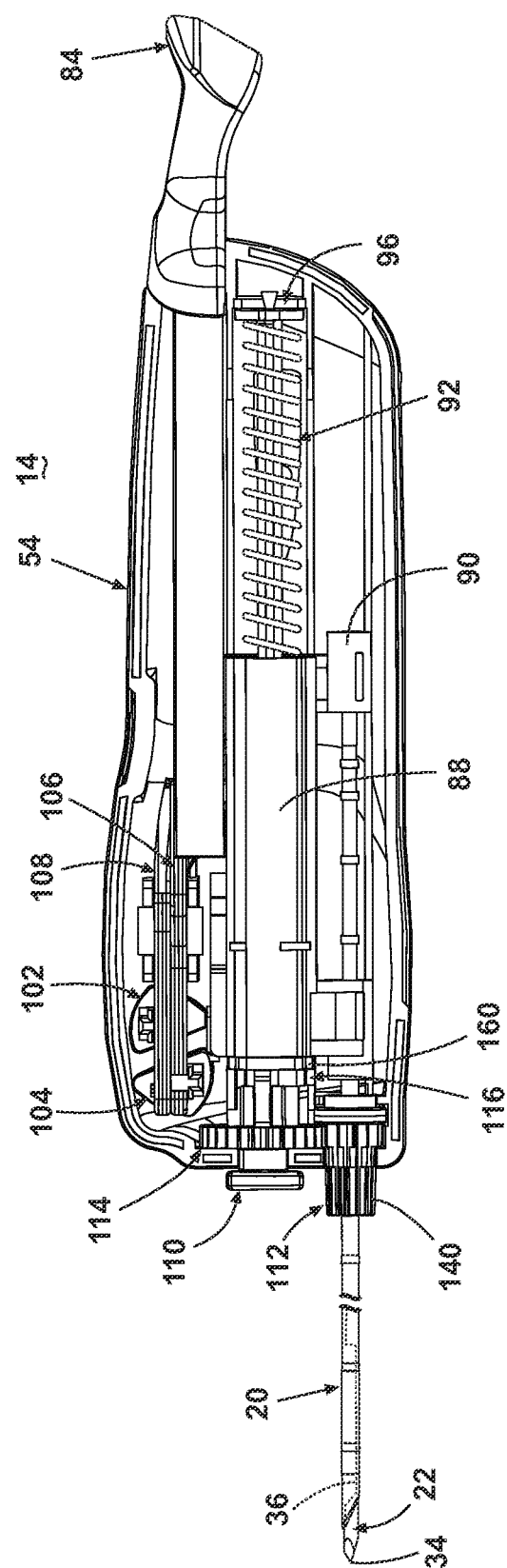
FIG. 9 is a longitudinal section of the biopsy device from FIG. 1 showing the biopsy device in the uncocked or fired position.
Figure 10:
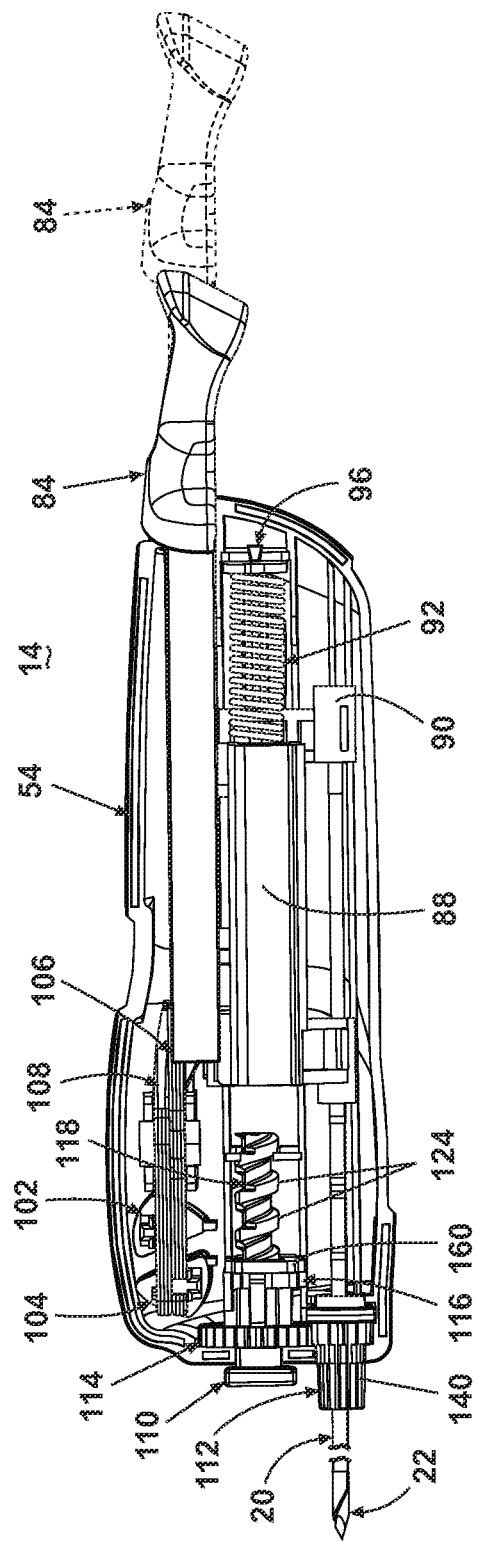
FIG. 10 is a longitudinal section of the biopsy device from FIG. 1 showing the biopsy device in the cocked or armed position.

Referring to FIG. 3, the cocking/firing assembly 42 comprises a cocking element 84, a cocking element spring 86, a cannula carriage 88 which carries the cannula 20, a stylet carriage 90 which carries the stylet 22, a cannula spring 92, a stylet spring 94, and a spring guide 128. The cocking element 84 is slidably mounted to the outer housing 40 for movement between a first, retracted position (FIG. 9) and a second, extended position (shown in phantom in FIG. 10), which defines a single arming stroke of the biopsy device 10. As illustrated herein, in the first position, the cocking element 84 is retracted into the outer housing 40 by the spring 86 and in the second position; the cocking element 84 is extended in a proximal direction from the outer housing 40. The cannula and stylet carriages 88, 90 are sequentially engaged by the cocking element 84 to draw the carriages 88, 90, and therefore the cannula 20 and stylet 22, back to an armed position (FIG. 10). The cannula and stylet carriages 88, 90 each have a respective retaining member or catch 98, 100 that releasably locks the carriages 88, 90 in the armed position relative to the outer housing 40. The spring guide 128 mounts the springs 92, 94, which act to bias the cannula and stylet carriages 88, 90 to a fired position (FIG. 9). The cannula carriage 88 can be laterally offset from the operational axis X in the first lateral direction A and the stylet carriage 90 can be laterally offset from the operational axis X in the second lateral direction B.

The trigger assembly 44 comprises a first button 102, a second button 104, a cannula retainer 106 and a stylet retainer 108. The first button 102 functions to fire the stylet 22 alone. The second button 104 functions to sequentially fire the stylet 22 and the cannula 20 in rapid succession, or, if the stylet 22 has already been fired via the first button 102, fire the cannula 20 alone. The cannula retainer 106 is operably coupled between the second button 104 and the cannula carriage 88. The cannula retainer 106 engages the catch 98 formed on the cannula carriage 88 to releasably retain the cannula carriage 88 in the armed position. The cannula retainer 106 is configured to be moved into engagement with the catch 98 during the first arming stroke of the biopsy device 10. The stylet retainer 108 is operably coupled between the first button 102 and the stylet carriage 90. The stylet retainer 108 engages the catch 100 formed on the stylet carriage 90 to releasably retain the stylet carriage 90 in the armed position. The stylet retainer 108 is configured to be moved into engagement with the catch 100 during the second arming stroke of the biopsy device 10.

Figure 7:
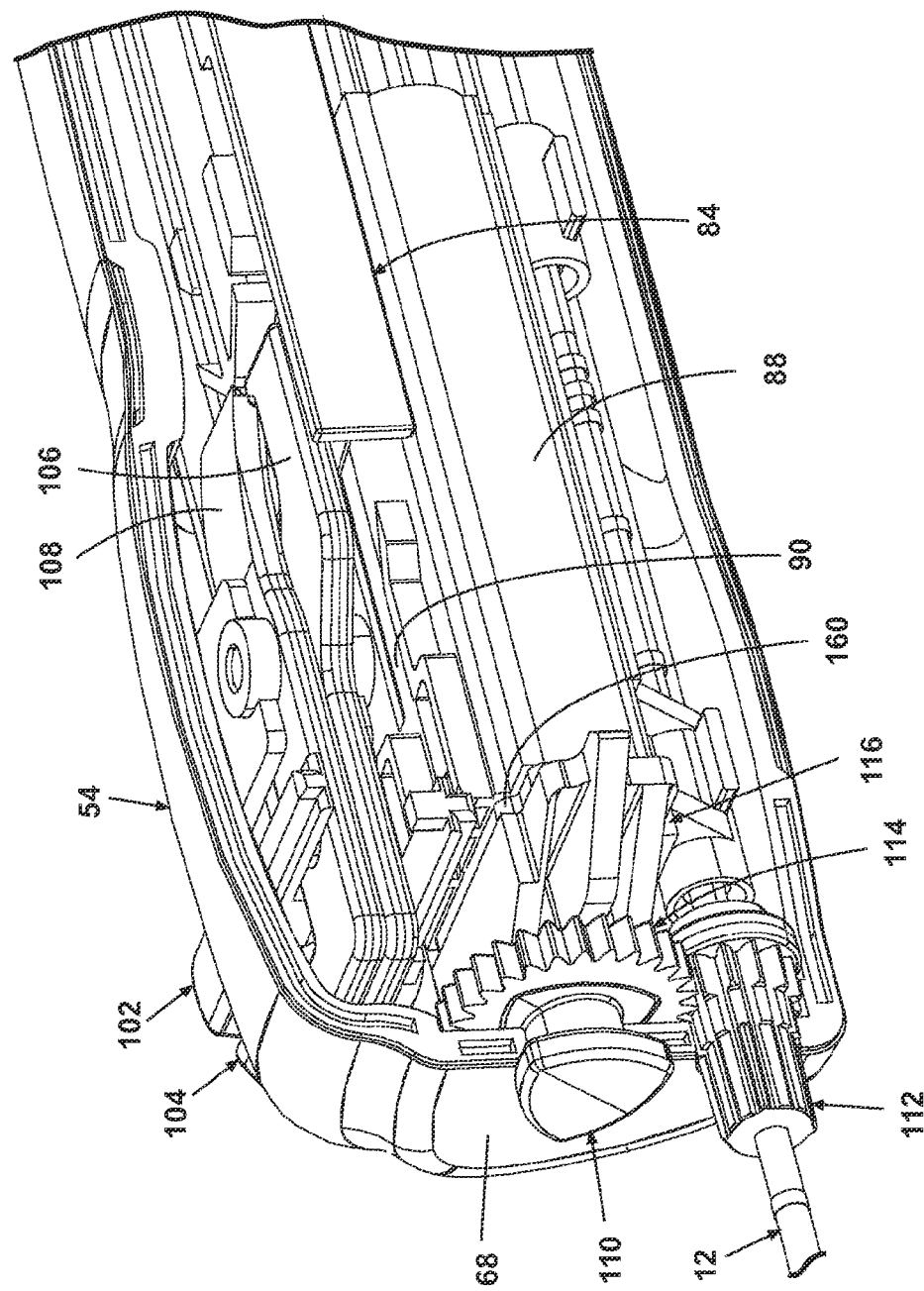
FIG. 7 is a perspective view of the biopsy device illustrated in FIG. 1 with the right housing shell removed to illustrate a sample size control assembly of the actuator assembly.
Figure 8:
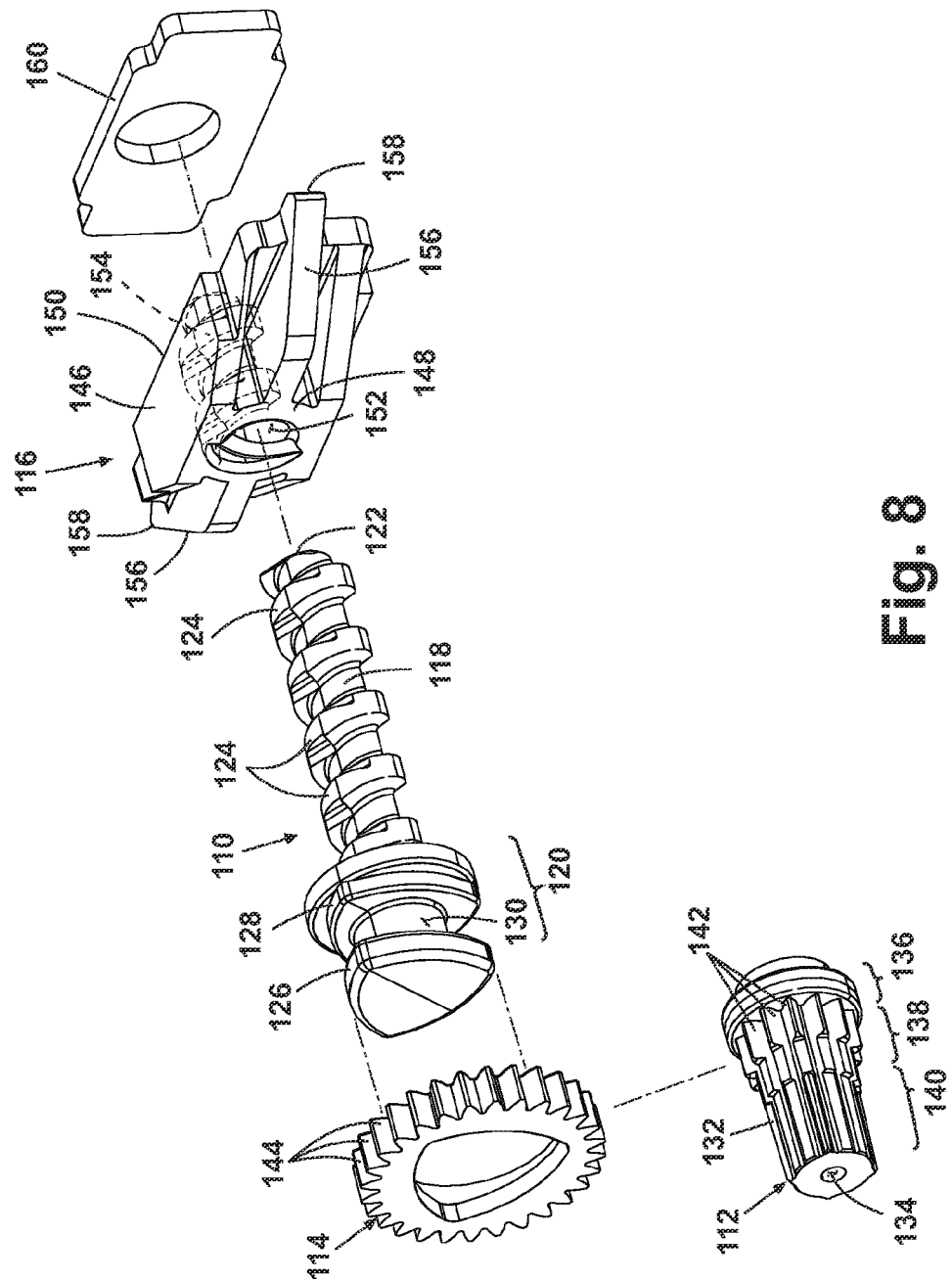
FIG. 8 is an exploded view of the sample size control assembly.

Referring to FIGS. 7 and 8, the sample size control assembly 46 comprises an adjusting member 110, an adjuster wheel 112, a gear 114 coupling the adjuster member 110 and the adjusting wheel 112, and a throw stop 116 coupled to the adjusting member 110. The throw stop 116 is linearly moveable along the adjusting member 110. The location of the throw stop 116 relative to the outer housing 40 will determine the distance the carriages 88, 90 can travel and consequently can determine the fired position of the carriages 88, 90.

The adjusting member 110 is an elongated, somewhat nail-shaped member comprising a cylindrical shaft 118 terminating in a distal mounting end 120 and a proximal end 122, with external threads 124 formed on the cylindrical shaft 118 between the ends 120, 122. The distal mounting end 120 comprises a pair of spaced flanges 126, 128 forming a space 130 therebetween which is received in the upper aperture 74 (FIG. 6) of the outer housing 40 such that the flange 126 is positioned exteriorly of the distal wall 68 and the flange 128 is positioned interiorly of the distal wall 68.

The adjuster wheel 112 comprises an annular body 132 defining an open-ended channelway 134 through which the needle assembly 12 extends. The annular body 132 includes mounting portion 136, a gear portion 138, and a nose portion 140. The annular body 132 is positioned within the chamber 78 (FIG. 6) with the mounting portion 136 received by the retainer wall 80 and the nose portion 140 projecting through the lower aperture 76. The gear portion 138, which includes a plurality of teeth 142 projecting outwardly from the annular body 132, is located within the chamber 78. Since the adjuster wheel 112 projects at least partially from the distal end of the housing 40, it can be considered a "nose" of the biopsy device 10. Also, since the adjuster wheel 112 operates the sample size control assembly 46, it can be considered an "actuator" of the sample size control assembly 46.

The gear 114 circumscribes the flange 128 of the adjusting member 110 and comprises outwardly projecting teeth 144 that mate with the teeth 142 formed on the adjuster wheel 112 to couple the adjuster wheel 112 to the adjusting member 110.

The throw stop 116 comprises a moveable body 146 having a distal face 148 and a proximal face 150 and defining an open ended channelway 152 extending between the distal and proximal faces 148, 150. A set of internal threads 154 extends along the channelway 152 and receive the external threads 124 on the adjusting member 110. The proximal face 150 can serve as a stop surface which the cannula and stylet carriages 88, 90 will strike when the biopsy device 10 is fired. Therefore, the location of the throw stop 116 relative to the outer housing 40 will determine the distance the cannula and stylet carriages 88, 90 can travel relative to the outer housing 40.

The body 146 further includes a pair of laterally extending wedge-like wings 156, each wing 156 having an outer tip 158. The body 146 is received in the channels 85 of the housing shells 52, 54, between the guide rails 70, 72, with the tips 158 visible in the indicator windows 82 (FIG. 6). The tips 158 can indicate the position of the throw stop 116 relative to the outer housing 40, which in turn can indicate either the throw distance the biopsy device is set to or the specimen size the biopsy device is set to collect since the position of the throw stop 116 determines the distance the cannula and stylet carriages 88, 90 can travel relative to the outer housing 40.

A damper 160 can optionally be provided on the throw stop 116 to provide noise dampening, vibration dampening, and/or shock absorption. As illustrated herein, the damper 160 comprises a relatively flat member located on the proximal face of the throw stop 116, in which case the cannula and stylet carriages 88, 90 will strike the proximal face of the damper 160 when fired. The damper 160 can be attached to the throw stop 116 using a pressure sensitive adhesive. The damper 160 can be fabricated from a material that provides noise dampening, vibration dampening, and/or shock absorption when contacted by the stylet carriage 90 and the cannula carriage 88, such as a polyurethane foam. The damper 160 can be configured to dampen the noise associated with firing the biopsy device 10. Optionally, the damper 160 can limit the noise to a level below that which triggers the acoustic startle reflex (also known as the acoustic startle response, both abbreviated as "ASR"), which is a reflex pattern or response a sudden unexpected stimulus, such as a loud noise, in the average human or in the majority of humans. Optionally, the damper 160 can limit the noise to under 115 decibels.

The operation of the biopsy device 10 generally comprises the steps of: (I) cocking or arming the biopsy device 10; (II) selecting the specimen size to be collected, i.e. setting the throw; (III) firing the biopsy device 10 to collect a specimen; and (IV) retrieving the specimen from the biopsy device. It will be apparent to one of ordinary skill that the operation procedure can proceed in any logical order and is not limited to the listed sequence. The arming step (I), firing step (III), and retrieving step (IV) are not germane to the invention, and will not be described further herein except for the effect specimen size selection step (II) has on the firing step (III).

Referring to FIGS. 9 and 10, the biopsy device 10 is initially in an uncocked or fired condition, shown in FIG. 9, and is typically cocked or armed prior to introducing the needle assembly 12 into the tissue mass 16 (FIG. 1). In the uncocked condition, the cocking element 84 is urged distally to the first position by influence of the cocking element spring 86 and the carriages 88, 90 are urged distally against the damper 160 by their respective springs 92, 94. The cocking element 84 is pulled rearwardly or proximally twice to sequentially retract the cannula carriage 88 and the stylet carriage 90 to the armed position, shown in FIG. 10, with the retaining catches 98, 100 engaging the retainers 106, 108 to releasably retain the carriages 88, 90 in the armed position.

Referring to FIG. 9, prior to or after the arming step (III), the specimen size to be collected is selected using the sample size control assembly 46. The adjuster wheel 112 is rotated to select the size of the biopsy sample the biopsy device 10 will collect. The nose portion 140 of the adjuster wheel 112 can be engaged directly by the user for manual rotation. Rotation of the adjuster wheel 112 is transmitted to the adjusting member 110 by the gear 114. The rotation of the adjusting member 110 is in turn translated to linear movement of the throw stop 116 along the cylindrical shaft 118. The throw stop 116 will move distally or proximally depending on the direction in which the adjustment wheel 112 is rotated. Indicia (visible in FIG. 1) can be provided as markings on the outer surface of the actuator assembly 14 adjacent the indicator window 82 to indicate various throw distances or specimen sizes that can be collected by the biopsy device 10, with the outer tips 158 of the throw stop 116 indicating the throw distance or specimen length that the biopsy device 10 is set to take. Since the sample size control assembly 46 relies upon translating rotational motion to linear motion, the throw can be infinitely adjusted. Optionally, the throw can be infinitely adjusted between 10 and 25 mm.

Figure 11:
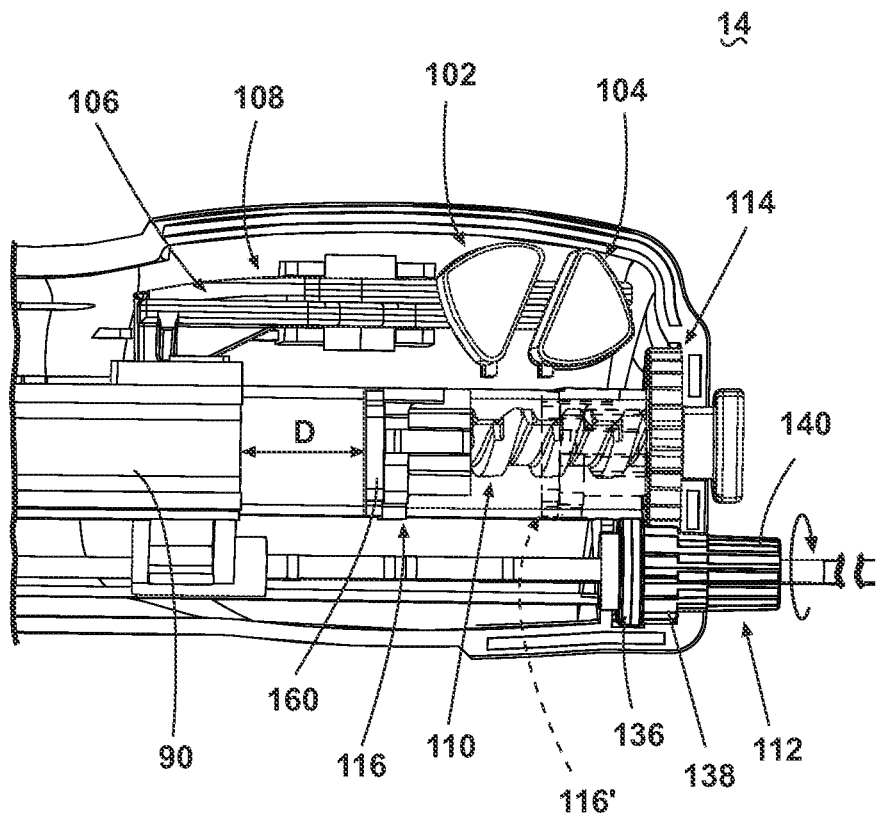
FIG. 11 is a side view of the sample size control assembly, illustrating the specimen size to be collected by the biopsy device being selected.
Figure 12:
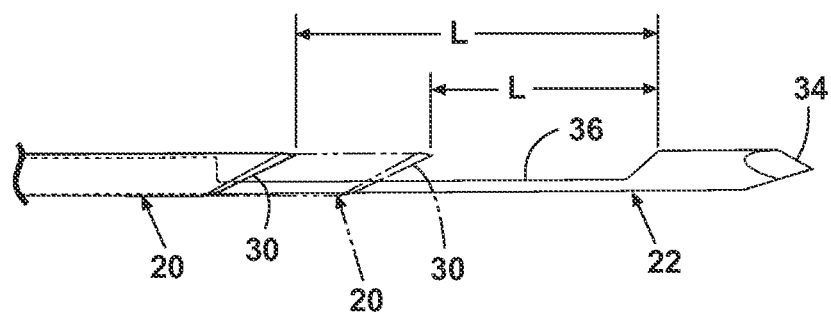
FIG. 12 is a view illustrating the cannula assembly with the stylet in the fired position.

Referring to FIGS. 11 and 12, when fired in accordance with the firing step (III), the cannula and stylet carriages 88, 90 will strike the damper 160 on the throw stop 116. Therefore, the location of the throw stop 116 relative to the outer housing 40 determines the distance the carriages 88, 90 travel, and consequently determines the fired positions of the carriages 88, 90. Because the stylet 22 is fixed to the stylet carriage 90, the stylet 20 will travel into the lesion 18 a distance equal to the distance between the damper 160 and the stylet carriage 90 in the armed position. The distance the stylet 20 travels when fired is referred to as the throw of the biopsy device 10. Thus, the sample size control assembly 46 can also be characterized as adjusting the throw of the biopsy device 10. The distance D between the damper 160 and the distal end of the stylet carriage 90, which can be set using the sample size control assembly 46, is equal to the throw of the biopsy device and is proportional to the specimen length the biopsy device 10 will collect. The throw of the biopsy device 10 determines the exposure length of the notch 36, i.e. the amount of notch 36 that is exposed beyond the cutting edge 30 before the cannula 20 is advanced over the stylet 22 to sever the sample. The length L of a collected specimen is generally equal to the exposure length of the notch 36. Therefore, a longer throw or greater distance D will produce a specimen having a greater length L.

Figure 13:
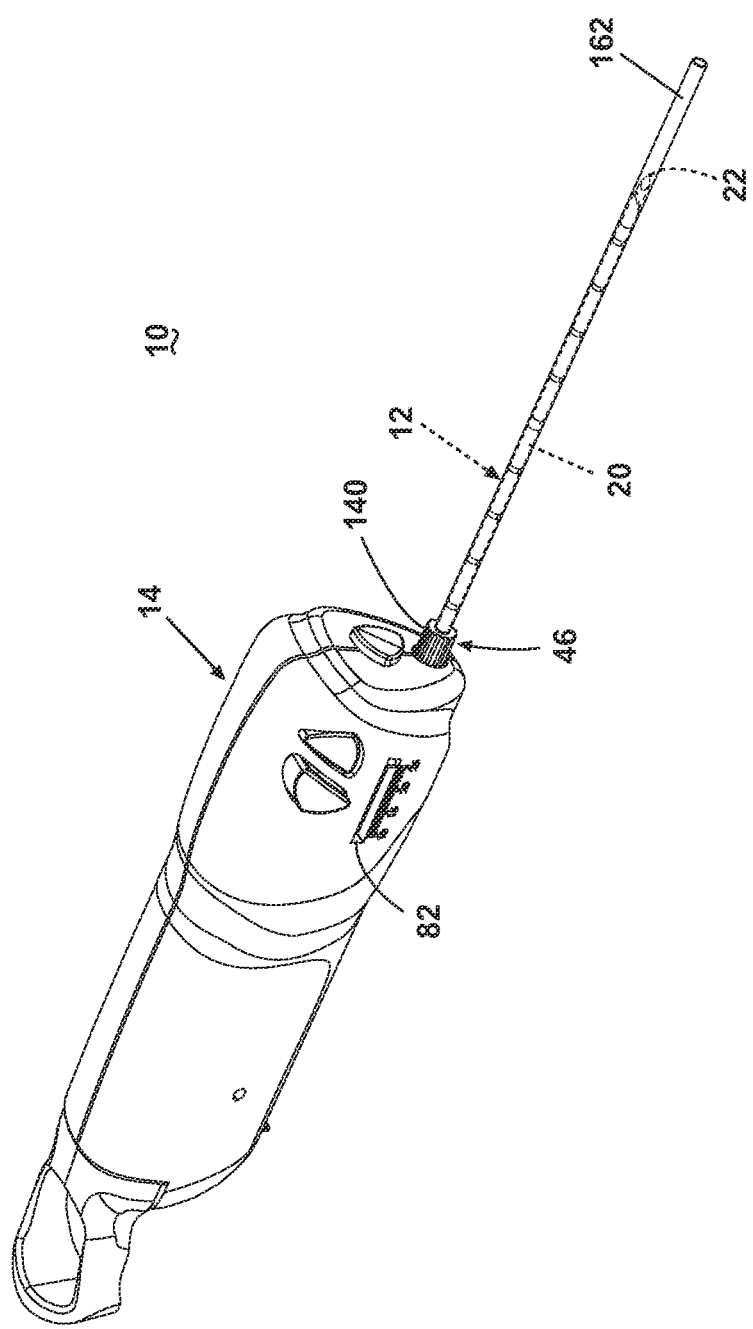
FIG. 13 is a perspective view of the biopsy device of FIG. 1 further comprising a tip protector for the cannula assembly which can be used to set the sample size.
Figure 14:
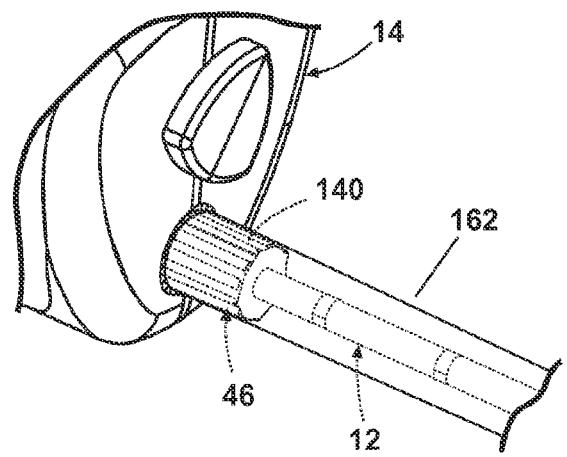
FIG. 14 is a close-up perspective view of a portion of the biopsy device of FIG. 13, illustrating a first exemplary coupling between the tip protector and the sample size control assembly.
Figure 15:
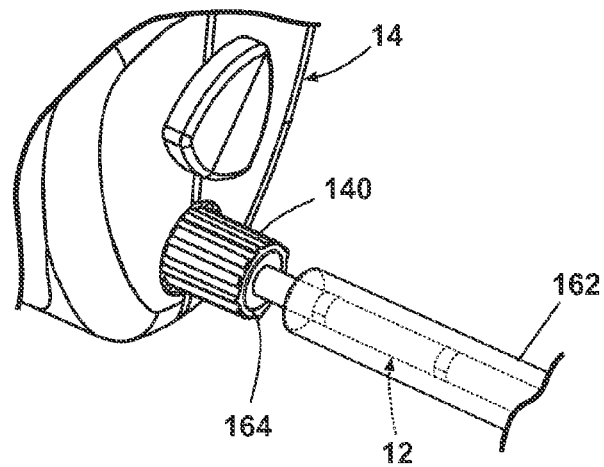
FIG. 15 is a close-up perspective view of a portion of the biopsy device of FIG. 13, illustrating a second exemplary coupling between the tip protector and the sample size control assembly.

Alternately, as shown in FIGS. 13-15, a tip protector 162, which is a sleeve-like device commonly used to cover the needle assembly 12 when not in use, can be removably coupled to the sample size control assembly 46, whereby movement of the tip protector 162 can be transmitted to the sample size control assembly 46 through the coupling to select the specimen size to be collected. As shown in FIG. 13, a proximal end of the tip protector 162 can couple with the nose portion 140, and the tip protector 162 can be engaged directly by the user for manual rotation, which is transmitted to the adjuster wheel 112 (FIG. 11) by the coupling between the tip protector 162 and the nose portion 140.

Figure 16:
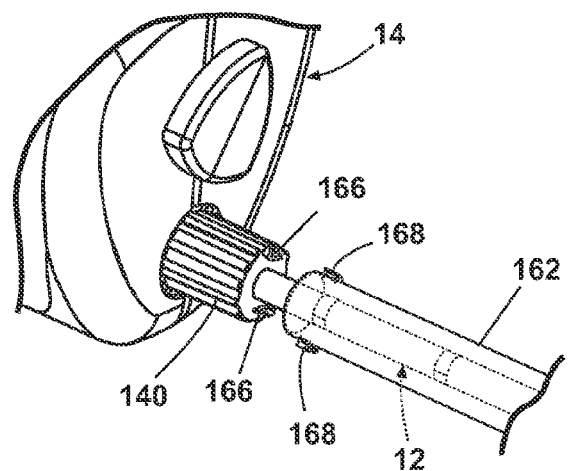
FIG. 16 is a close-up perspective view of a portion of the biopsy device of FIG. 13, illustrating a third exemplary coupling between the tip protector and the sample size control assembly.

Any suitable coupling between the tip protector 162 and the sample size control assembly 46 can be employed. One example of a suitable coupling is shown in FIG. 14, wherein a proximal end of the tip protector is temporarily press fit over the nose portion 140. Friction between the tip protector 162 and the nose portion 140 will transmit rotational movement of the tip protector 162 to the nose portion 140. A second example is shown in FIG. 15, wherein the nose portion 140 comprises a groove 164 that receives the proximal end of the tip protector 162. A third example is shown in FIG. 16, wherein the coupling comprises a Luer-type locking arrangement, with first hooks 166 provided on the nose portion 140 and second hooks 168 provided on the tip protector 162 that are engageable with the first hooks 166.

Using the tip protector 162 to set the sample size is advantageous because it may be easier for some users to manipulate the larger tip protector 162 rather than the smaller nose portion 140, and the needle assembly 12 is safely covered during adjustment.

While the invention has been specifically described in connection with certain specific embodiments thereof, it is to be understood that this is by way of illustration and not of limitation. For example, it is understood that the sample size control assembly of the invention could be used with a biopsy device having a coring cannula and a non-notched stylet. In such a variation, the throw distance of the core biopsy device would be the distance the coring cannula travels past the stylet. The sample size would be roughly equal to the distance the distal edge of the coring cannula projects past the distal tip of the stylet when fired. The throw stop would function to arrest the movement of the cannula, such as by stopping a cannula carriage carrying the cannula. Other reasonable variations and modifications are possible within the scope of the forgoing disclosure and drawings without departing from the spirit of the invention which is defined in the appended claims.

What is claimed is:
1. A biopsy device for percutaneous removal of a specimen from a tissue mass, the biopsy device comprising:
    a housing having a proximal end and a distal end;
    a sample size control assembly for selecting a size of the specimen to be collected comprising:
        an adjusting member provided within the housing;
        a nose rotatably mounted to the housing and projecting from the distal end; and
        a throw stop coupled to the adjusting member;

a cannula defining a lumen having a distal end and extending through the nose;

a cannula carriage provided within the housing for movement relative to the housing and coupled to the cannula;

a stylet having a notch and extending through the lumen;

a stylet carriage provided within the housing for movement relative to the housing, and coupled to the stylet; and a firing assembly carried by the housing and operably coupled to the cannula and stylet carriages, wherein the firing assembly is configured to relatively move the cannula and the stylet from an armed position, where the cannula and stylet carriages are spaced from the throw stop and the cannula covers the notch, through an intermediate position, where the stylet carriage abuts the throw stop and the notch extends at least partially beyond the distal end of the cannula, and to a fired position, where both the cannula and stylet carriages abut the throw stop and the cannula covers the notch;

wherein the stylet travels a distance between the armed position and the intermediate position, the distance defining a throw distance that is related to the specimen size and the nose is operably coupled to the adjusting member such that rotation of the nose actuates the adjusting member to move the throw stop within the housing to adjust the throw distance, and thereby adjust the specimen size.

2. The biopsy device from claim 1, wherein the housing has opposing channels, and the throw stop is moveable within the channels.

3. The biopsy device from claim 1, wherein the housing comprises at least one window, and the throw stop comprises a portion visible in the at least one window.

4. The biopsy device from claim 3 and further comprising indicia on an exterior surface of the housing adjacent the at least one window that indicates at least one of the throw distances and the specimen sizes that can be collected by the biopsy device.

5. The biopsy device from claim 4, wherein the portion of the throw stop visible in the window indicates one of the throw distance and the specimen size the biopsy device is set to obtain.

6. The biopsy device from claim 1, wherein the throw stop is coupled to the adjusting member such that rotation of the adjusting member is translated to linear movement of the throw stop relative to the housing.

7. The biopsy device from claim 6, wherein the adjusting member comprises external threads, and the throw stop comprises internal threads that receive the external threads of the adjusting member.

8. The biopsy device from claim 1, wherein the nose comprises a portion interior of the housing that is operably coupled to the adjusting member.

9. The biopsy device from claim 8, wherein the sample size control assembly further comprises a gear operably coupling the adjusting member and the portion interior of the housing.

10. The biopsy device from claim 9, wherein the adjusting member comprises external threads, and the throw stop comprises internal threads that receive the external threads of the adjusting member, and the gear circumscribes the adjusting member.

11. The biopsy device from claim 1 and further comprising a damper provided between the throw stop and the carriages.

12. The biopsy device from claim 1 and further comprising a removable tip protector extending at least partially over the cannula and coupled to the sample size control assembly.

* * * * *